United States Patent [19]

Smith

[11] Patent Number: 4,839,295
[45] Date of Patent: Jun. 13, 1989

[54] MEASUREMENT OF PROTEIN USING BICINCHONINIC ACID

[75] Inventor: Paul K. Smith, Roscoe, Ill.

[73] Assignee: Pierce Chemical Company, Rockford, Ill.

[21] Appl. No.: 53,708

[22] Filed: May 26, 1987

Related U.S. Application Data

[63] Continuation of Ser. No. 618,727, Jun. 8, 1984, abandoned.

[51] Int. Cl.$^4$ ............................................. G01N 33/68
[52] U.S. Cl. ......................................... 436/86; 436/88
[58] Field of Search ....................... 436/80, 86, 87, 88, 436/164

[56] References Cited

FOREIGN PATENT DOCUMENTS 126295  1/1960  U.S.S.R. .................................. 436/80

OTHER PUBLICATIONS

Lowry et al; J. Biol. Chem. 193, 265–275.
Gindler–The Cu-2,2'-Bicinchoninate System, American Medical Tech. Nat'l Meeting; Denver, CO. Jul. 1970.

Primary Examiner—Michael S. Marcus
Attorney, Agent, or Firm—Connolly, Oliver, Close & Worden

[57] ABSTRACT

$Cu^+$ produced during the reaction of protein with alkaline $Cu^{++}$ can be monitored by measuring the absorbance at 562 nm of the intense purple complex formed with the ion of bicinchoninic acid (BCA). The color produced is stable and increases in a linear fashion over a broad working range of increasing protein concentration. Since BCA is stable, it is incorporated in the reagent formulation at the start of the reaction. Thus, the method offers mechanical simplification over the method described by Lowry et al.

1 Claim, No Drawings

MEASUREMENT OF PROTEIN USING BICINCHONINIC ACID

This is a continuation of application Ser. No. 618,727, filed June 8, 1984, now abandoned.

The widely used Lowry et al., method (J. Biol. Chem. 193, 265275) for protein measurement relies on the Folin-Ciocalteau reagent (phosphomolybdic-tungstic mixed acid) to "measure copper-treated protein produced in the biuret reaction". The instability of the Folin-Ciocalteau reagent in the alkaline biuret reaction medium demands that good technique be exercised in the timing of addition and mixing of reagent with sample. The reagent instability also limits the linear working range of the Lowry assay requiring occasional dilution and re-assay of certain samples. An additional potential drawback of the Folin-Ciocalteau reagent is that color is generated from tyrosine and tyrptophan residues as well as "that produced by the biuret reaction". This fact may contribute some spurious protein-to-protein variability.

The Coomassie dye binding technique for protein measurement introduced by Bradford (anal. Biochem. 72, 248-254) offers mechanical simplicity and freedom from a wide range of interferences, but suffers in that the variation of response from protein-to-protein can be rather large. A further limitation of the Coomassie dye binding assay is that many protein samples are difficult or impossible to dissolve in the acidic Bradford system.

The present invention provides a method for measuirng protein concentration in a fluid sample which has distinct advantages over either the Lowry et al., method or the Bradford dye binding technique. A source of $Cu^{++}$ is added to the fluid sample and the protein therein reduces $Cu^{++}$ to $Cu^{+}$. The present invention then the ion of bicinchoninic acid (BCA) to monitor the amount of $Cu^{+}$ formed. Bicinchoninic acid is used in the form of a water soluble salt. When dissolves, the BCA ion combines with $Cu^{+}$ and forms an intense purple colored complex, the absorbance of which can be read at 562 nm.

While the ion of BCA is known to be a sensitive, stable, and specific reagent for $Cu^{+}$ (Zh. Anal. Khim 20, 390-392) and has been used to monitor substance capable of reducing $Cu^{++}$ such as uric acid and glucose (Clin. Chem. 16, 519 and 536), no where are the advantages accompanying its use in a protein assay evident. These advantages include:

Over Lowry et al.,
(1) mechanical simplification since the two step, separate, timed addition of detection reagent is not needed—BCA is stable and can be incorporated in a reagent formuation containing $Cu^{++}$ prior to the addition of the protein,
(2) an expanded linear working range without sacrificing sensitivity, and
(3) less color generation from tyrosine or tryptophan residues;

Over Bradford,
(1) considerably less protein-to-protein variation, and
(2) the ability to be used in an alkaline environment.

The present invention can be practiced in the following manner.

Bicinchoninic acid, as its water soluble sodium salt, can be prepared by the Pfitzinger reaction of isatin and acetoin using the method of Lesene and Henze (J. Amer. Chem. Soc. 64, 1897-1900) with the substitution of sodium hyroxide for potassium hydroxide. The crude product so obtained is subjected to at least three recrystallizations from a minimun amount of 75° C. water. Upon drying at 60° C., the anhydrous BCA salt is an amorphous, cream colored powder.

Using this BCA salt, an aqueous BCA reagent solution is prepared containing, by weight, 1% of the BCA salt, 2% $Na_2CO_3H_2$), 0.16% Na tartrate, and 0.4% NaOH. The inorganic salts are of reagent quality grade. The carbonate and hydroxide are buffer constituents with the tartrate being present to thereafter complex with $Cu^{++}$ to maintain this ion in solution. In preparing this aqueous solution, deionized water (18 megohm-cm) delivered from all plastic cartridge unit should be used to avoid copper contamination. To remove any insoluble debris, the solution is filtered through 1 micron filters.

To prepare a Working Reagent, one part by weight of a 4% $CuSo_4\ 5H_2O$ solution (prepared with deionized water and filtered as above described) is mixed with 100 parts of the BCA reagent. The absorbance blank at 562 nm of the Working Reagent should be less than 0.065. If it is greater, than a new Working Reagent should be prepared using a BCA salt which has been further purified by additional recrystallization. In order to enhance protein solubility where necessary, a small amount (0.1%) of surfactant such as SDS can be added to the Working Reagent.

To use the Working Reagent for the measurement of protein, 2 ml of the Working Reagent can be added to a vial which contains 100 ul of a fluid sample which contains 0–2000 ug of the protein of interest. Incubation of the vial in a water bath at 60° C. for 30 minutes assures a stable end point of the reaction and achieves maximum sensitivity. After the vial has cooled to room temperature, absorbance is read at 562 nm. In like fashion, a calibration curve can also be constructed for the protein of interest from standard solutions containing 0–2000 ug of the protein per ml. The amount of protein in the sample is then determined by comparison of the obtained absorbance with those on the calibration curve.

While the present invention has been illustrated with respect to a sample wherein the protein to be measured is in solution, the method, because it utilizes a colored reaction complex which is small and very soluble, can also be used in instances where the protein is immobilized on an insoluble support such as agarose.

I claim:
1. A method for measuring protein concentration in a fluid containing protein comprising the steps of:
 (a) combining the fluid with an alkaline aqueous reagent system containing $Cu^{++}$ and the ion of bicinchoninic acid, whereupon $Cu^{++}$ is reduced to $Cu^{+}$ in proportion to the amount of protein present in the fluid and said $Cu^{+}$ so produced combined with said ion of bicinchoninic acid to form a purple colored complex;
 (b) measuring the absorbance of said colored complex; and
 (c) determining the protein concentration in the fluid by comparing the measured absorbance with the absorbance obtained on measurements of fluid samples containing known concentrations of protein.

* * * * *